United States Patent [19]

Klein

[11] 4,210,154

[45] Jul. 1, 1980

[54] SLEEVE WITH ARMBAND

[75] Inventor: Johann Klein, Cologne, Fed. Rep. of Germany

[73] Assignee: Bayer Aktiengesellschaft, Leverkusen, Fed. Rep. of Germany

[21] Appl. No.: 857,963

[22] Filed: Dec. 6, 1977

[30] Foreign Application Priority Data

Dec. 18, 1976 [DE] Fed. Rep. of Germany ....... 2657519

[51] Int. Cl.$^2$ .............................................. A61B 5/02
[52] U.S. Cl. ...................................... 128/685; 128/686
[58] Field of Search ................ 128/2.05 A, 2.05 M, 128/2.05 G, 2.05 C, 2.05 S, 327, DIG. 20, 679, 685, 686; 239/66

[56] References Cited

U.S. PATENT DOCUMENTS

| | | | |
|---|---|---|---|
| 1,043,521 | 11/1912 | Hoobler | 128/2.05 G |
| 1,729,297 | 9/1929 | Stewart | 128/2.05 C |
| 3,825,008 | 7/1974 | Shook | 128/327 |
| 4,026,468 | 5/1977 | Tinder et al. | 239/66 |

Primary Examiner—George J. Marlo
Attorney, Agent, or Firm—Sprung, Felfe, Horn, Lynch & Kramer

[57] ABSTRACT

A sleeve working in connection with electronic sphygmomanometers is provided with two separate inflatable pressure chambers of different size, which may be connected selectively to a suitable pressure source. A switch-over device is provided in the line to the pressure source for inflating either the first or the second pressure chamber. The two pressure chambers are adapted to the average diameter of a child's arm and adult's arm respectively.

4 Claims, 5 Drawing Figures

SLEEVE WITH ARMBAND

The invention relates to a sleeve with an armband for measuring blood pressure wherein the sleeve is wound around and fixed on a part of the patient's body, the sleeve having an inflatable pressure chamber.

Sleeves are known which are formed of textile materials and have a pressure chamber therein consisting of rubber. They are placed above the patient's elbow and inflated automatically or manually. The arteria brachialis is thus constricted to a certain extent. In addition to simply measuring the pulse frequency and the like, the sleeves, particlarly when connected to an automatic recording instrument, (see German Offenlegungsschrift No. 2,340,813.1), can be used to determine both the systolic and diastolic value of the associated pulse pressure by the Riva-Rocci/korotkoff method. These measurements are determined in a manner known per se by the appearance and disappearance of the Korotkoff noise which are related to the constriction and release of the constriction on the arteria brachialis.

The insertion of either a microphone or an acoustic chamber in the sleeve is known for transmitting the sound. In the latter case, there are two chambers in the sleeve, one chamber being the pressure chamber and the other chamber, which is substantially smaller, serving only to pick up the Korotkoff noise and convey it to a sound transducer in the recording instrument. The actual pressure chamber communicates with a control pump or another external pressure producer, for example a rubber bellows which inflates the pressure chamber and thus constricts the artery. The small sound chamber cannot fulfil this function as mentioned above.

Blood pressure is measured both on adults and on children and the dimensions of their arms differ so substantially that in the past it was necessary to use a different sleeve with different pressure chambers for an adult from that used for a child, because the adult's sleeve was too large for the child's arm and the sleeve for the child's arm was too small to be fastened correctly and to operate reliably on an adult. As maximum reliability was desired in measurement, even very small errors originating from poorly adapted sleeves were unacceptable. This is disadvantageous in that when changing from adults to children or vice versa, it is always necessary either to remove the sleeve tubes from the sleeve and reconnect them or, as is generally the case, to remove them from the pump and reconnect them. This is made more difficult particularly when using automatic recording instruments in which case the ends of the tubes are not easily accessible so as to afford better protection. More time is spent when carrying out series of examinations in particular when the patient's arms are of different sizes. Such waste of time cannot be tolerated in a modern doctor's practice.

The object of the invention is to avoid the above disadvantages and to provide a sleeve in which conversion of a sleeve from an adult's sleeve to a child's sleeve may take place practically in seconds.

In accordance with the invention there is provided a sleeve with an armband for measuring blood pressure wherein the sleeve which has an inflatable pressure chamber, is, in use wound and fixed round a part of the patient's body, the sleeve comprising a first pressure chamber, a separate second pressure chamber of different size to the first, and a pneumatic switch-over component for switching a supply of compressed air selectively to either chamber.

A considerable advantage in terms of saving in time can thus be obtained by being able to swtich from one pressure chamber to another pressure chamber on a single sleeve which is fixed permanently to the instrument or the pump.

Embodiments of the invention are shown in the accompanying drawings, in which.

Figure 1:
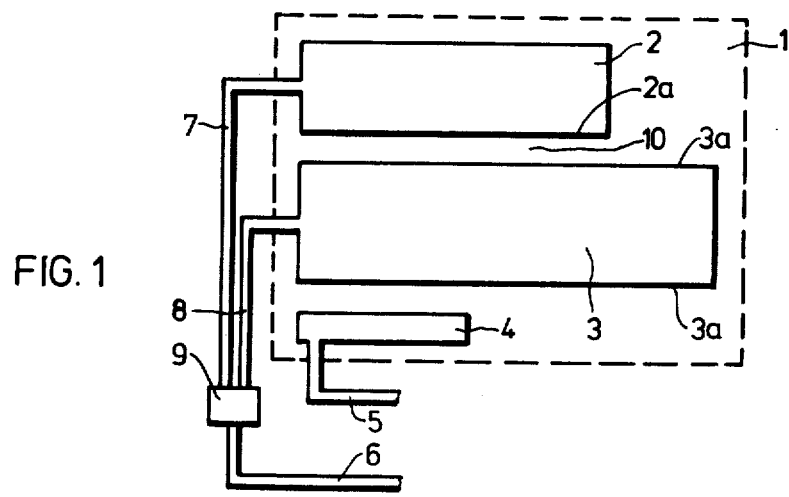
FIG. 1 shows a diagrammatic layout of two pressure chambers wherein an additional small acoustic chamber is provided in this case for detecting the sound.
Figure 2:
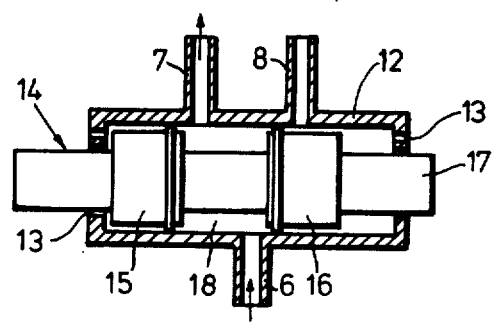
FIGS. 2 and 3 are diagrammatic side elevations of a switch-over component in the form of a slide piston.

The sleeve 1, the arm band and associated seal of which are omitted from FIG. 1, comprises a relatively small pressure chamber 2 for children, a larger pressure chamber 3 for adults, an acoustic chamber 4 having pneumatic pipes 5 which lead to a pressure measuring instrument or the like (not shown), and a pneumatic pipe 6 for the pressure chambers which leads to a pump or the like (not shown) by which the respective pressure chamber 2 or 3 is inflated when the sleeve is applied. At least one pneumatic switch 9 is located between the pipe 6 and the associated branch pipes 7 and 8 for the pressure chambers 2 and 3 respectively, and the structure of the switch can be seen in more detail in FIGS. 2 and 3. As shown in FIG. 1 the walls 2a and 3a of the chambers 2 and 3 respectively which are composed of sheets of rubber material, have a strip of material 10 of the sleeve between them for conveniently forming a fold, so that when the sleeve is wound up the walls 2a and 3a of the pressure chambers 2 and 3 respectively always fit closely together without deformation and folds of FIGS. 4 and 5. This ensures that each of the chambers 2 and 3 functions individually at an optimum and is not disturbed by the other chamber.

Figure 4:
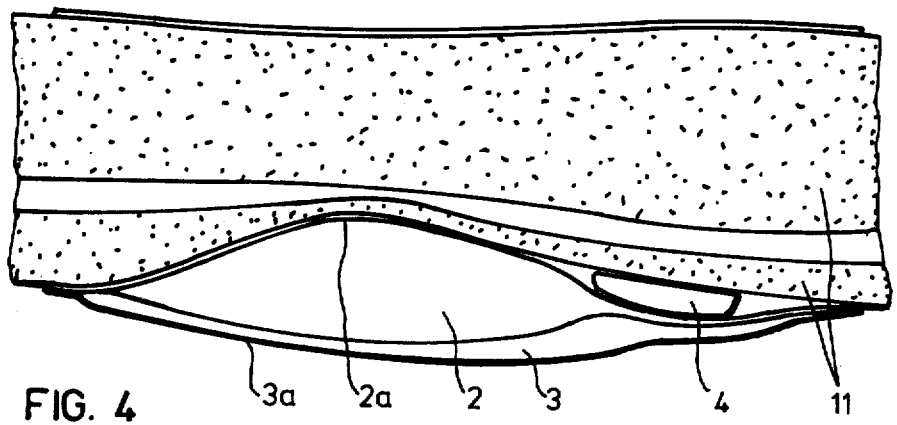
FIGS. 4 and 5 are diagrammatic cross-sections through a child's arm and an adult's arm respectively in which the smaller pressure chamber intended for the child is inflated in FIG. 4 and the larger pressure chamber intended for the adult is inflated in FIG. 5.
Figure 5:
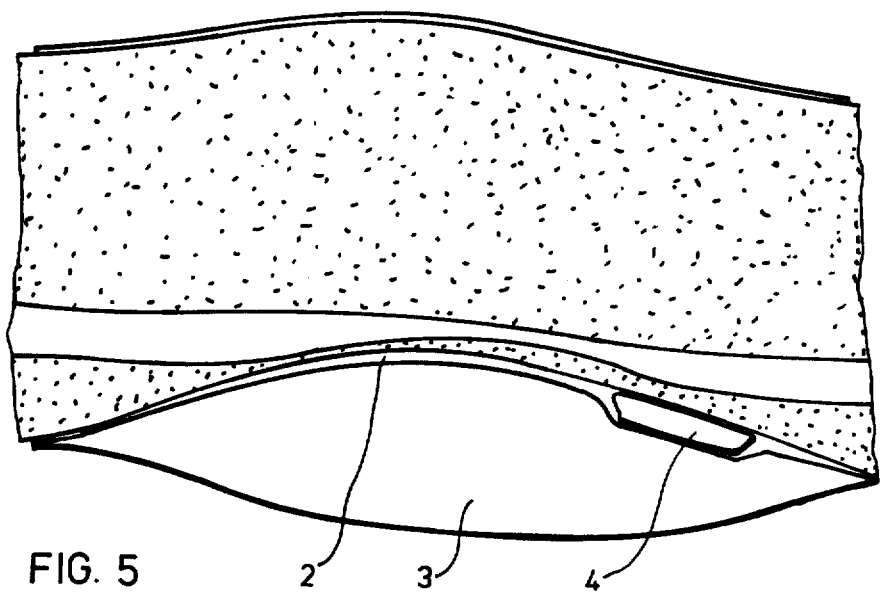

FIGS. 4 and 5 show that when the smaller chamber 2 is inflated, its wall 2a fits tightly on the child's arm 11 while the wall 3a of the other chamber 3 is not subjected to the pressure but does not interfere with the transfer. The reverse applies when chamber 3a is inflated but chamber 2 not inflated. FIGS. 4 and 5 also show that in each case the small acoustic chamber contacts either chamber 3 or chamber 2 so that the sound pressures corresponding to the Korotkoff noise can easily be fed to the chamber 4 and thence via the pipe 5 to the sound transducer. As shown in particular in FIGS. 4 and 5, the acoustic chamber 4 (if this is used instead of a microphone) is arranged in such a way that it always contacts a pressure chamber at least partially when the pressure chamber is inflated, cf. FIG. 4. The walls of the acoustic chamber 4 and part of a wall of a pressure chamber thus lie against each other at least partially when the sleeve is wound up.

The pneumatic switch 9 preferably has a housing 12, formed for example of plastic, having axial openings 13 through which a piston unit 14 is inserted. The piston unit 14 has piston members 15 and 16 in the manner of step pistons, which extend radially outwardly of a shaft 17 of the unit. The pistons may have a surrounding rubber seal on their circumference.

In a first position (FIG. 2) compressed air flows via the common feed pipe 6 via the communicating chamber 18 in the direction of the arrow and thence through the pipe 7 to chamber 2. In this case, the instrument is prepared for measurement on a child's arm.

Figure 3:
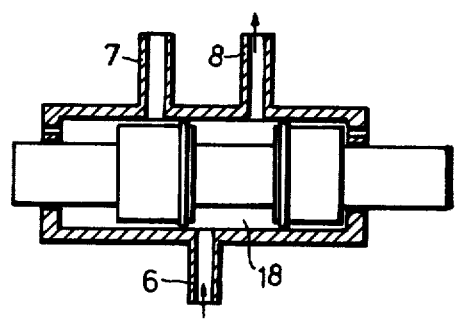

If the next patient is an adult the same sleeve is applied to his upper arm except that the shaft 17 of the piston is moved from left to right (FIG. 3). The compressed air now flows from the pump via the feed pipe 6, the communicating chamber 18 and the feed pipe 8 into the air-tight pressure chamber 3, which is thus inflated. The medical examination can now be carried out in known manner by controlling a pump valve to raise or lower the pressure in the pressure chamber 3 in a suitable manner.

Instead of the switch-over component being a slide piston, it may be a spring loaded or returning rocker, pivoting or press-button switch or an electromagnetic switch. The switch-over component may be rigidly fixed to a remote control instrument and form a structural unit.

What we claim is:

1. A sleeve with an armband for measuring blood pressure of the type which is wound and fixed round a part of the patient's body during use, the sleeve comprising a first inflatable longitudinal pressure chamber windable along its longitudinal axis about body parts having a first range of circumferential extent, a separate second inflatable longitudinal pressure chamber having a substantially greater length than the first windable along its longitudinal axis about body parts having a second range of circumferential extent different from the first, wherein the two chambers extend longitudinally superposed one upon the other, and pneumatic swtich-over means for swtiching a supply of compressed air alternatively to the first chamber when a body part having a circumferential extent in the first range is to be wound around or the second chamber when a body part having a circumferential extent in the second range is to be wound around to effect the inflation of only one of the two chambers while maintaining the other chamber in the deflated state.

2. A sleeve according to claim 1, wherein the switch-over means comprises a slide piston.

3. A sleeve for measuring blood pressure, comprising: means defining a first inflatable longitudinal pressure chamber having a first length and windable along it longitudinal axis about body parts having a first range of circumferential extent; means defining a second inflatable longitudinal pressure chamber having a second length substantially greater than said first length and windable along its longitudinal axis about body parts having a second range of circumferential extent different from the first and wherein said first chamber extends longitudinally with respect to the second chamber with the two chambers superposed one upon the other; and means receptive of compressed air for alternatively effecting the inflation of only the first chamber when a body part having a circumferential extent in the first range is to be wound around and the second chamber when a body part having a circumferential extent in the second range is to be wound around, while maintaining the other chamber in the deflated state.

4. The sleeve according to claim 3, wherein the means for inflating comprises a slide piston.

* * * * *